United States Patent [19]
Jurcik et al.

[11] Patent Number: 5,351,120
[45] Date of Patent: Sep. 27, 1994

[54] SPECTROSCOPIC CELL DESIGN

[75] Inventors: Benjamin Jurcik, Willowbrook; Michael Brandt, Chicago; Ronald Inman, Berwyn; James McAndrew, Lockport, all of Ill.

[73] Assignee: American Air Liquide, Walnut Creek, Calif.

[21] Appl. No.: 90,883

[22] Filed: Jul. 12, 1993

[51] Int. Cl.$^5$ .............................................. G01N 21/05
[52] U.S. Cl. ...................................... 356/246; 356/440
[58] Field of Search ....................... 356/246, 437, 440; 250/343

[56] References Cited
U.S. PATENT DOCUMENTS 3,989,938 11/1976 Auth ...................................... 356/346
4,749,276 6/1988 Bragg et al. ........................ 356/246
5,291,265 3/1994 Kebalsian ............................ 356/246

*Primary Examiner*—Richard A. Rosenberger
*Attorney, Agent, or Firm*—Malcolm B. Wittenberg

[57] ABSTRACT

The spectrographic sample cell for the analysis of trace impurities in sample gases. The cell is provided with a gas inlet, a gas outlet and a volume for confining the sample gases for analysis. Two mirrors are provided, a first mirror proximate the gas inlet the second mirror proximate the gas outlet, the first mirror having a hole at its radial center. A conically-shaped cell profile is further provided such that the formation of vortices of sample gas is prevented in the cell upstream of or in the region where the analysis of trace impurities is to take place.

14 Claims, 4 Drawing Sheets

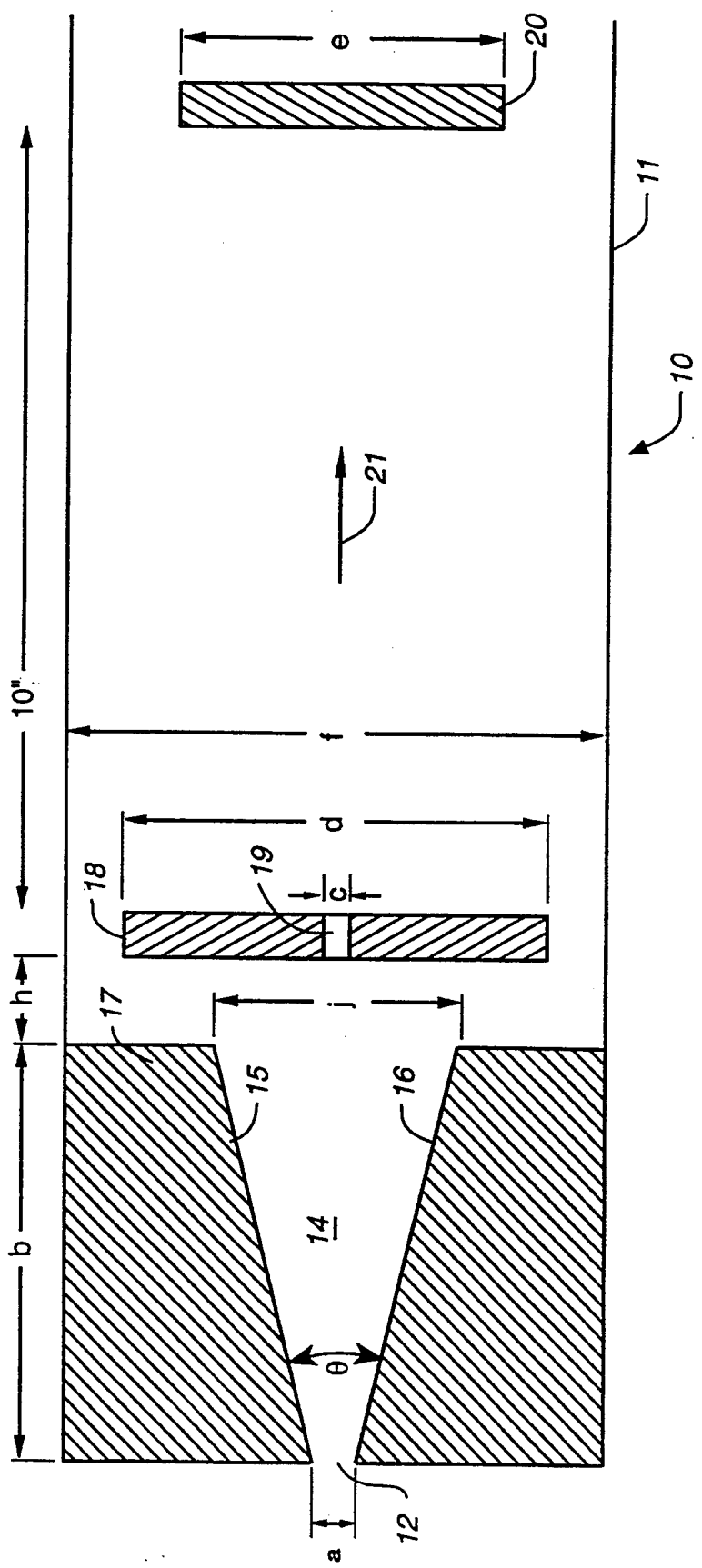
FIG._1

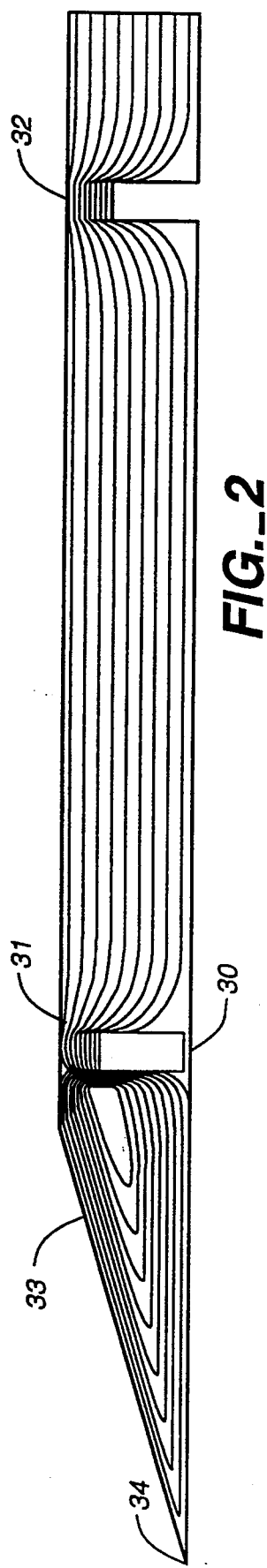
FIG._2
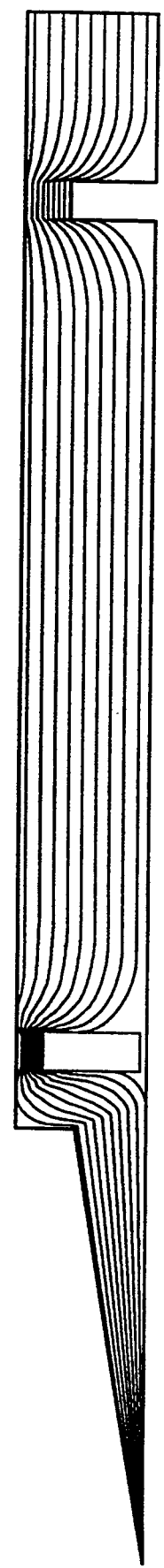
FIG._3

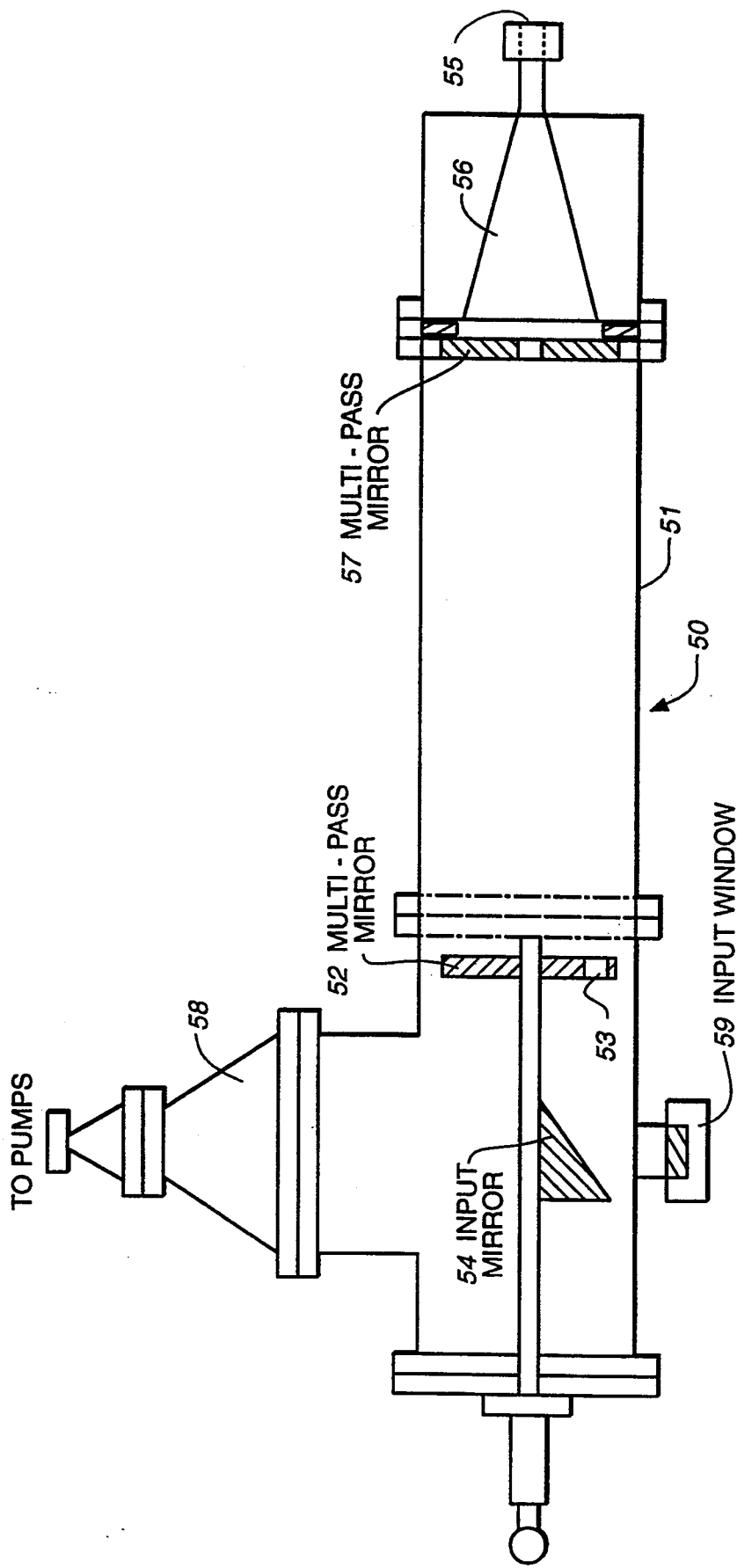
FIG._4

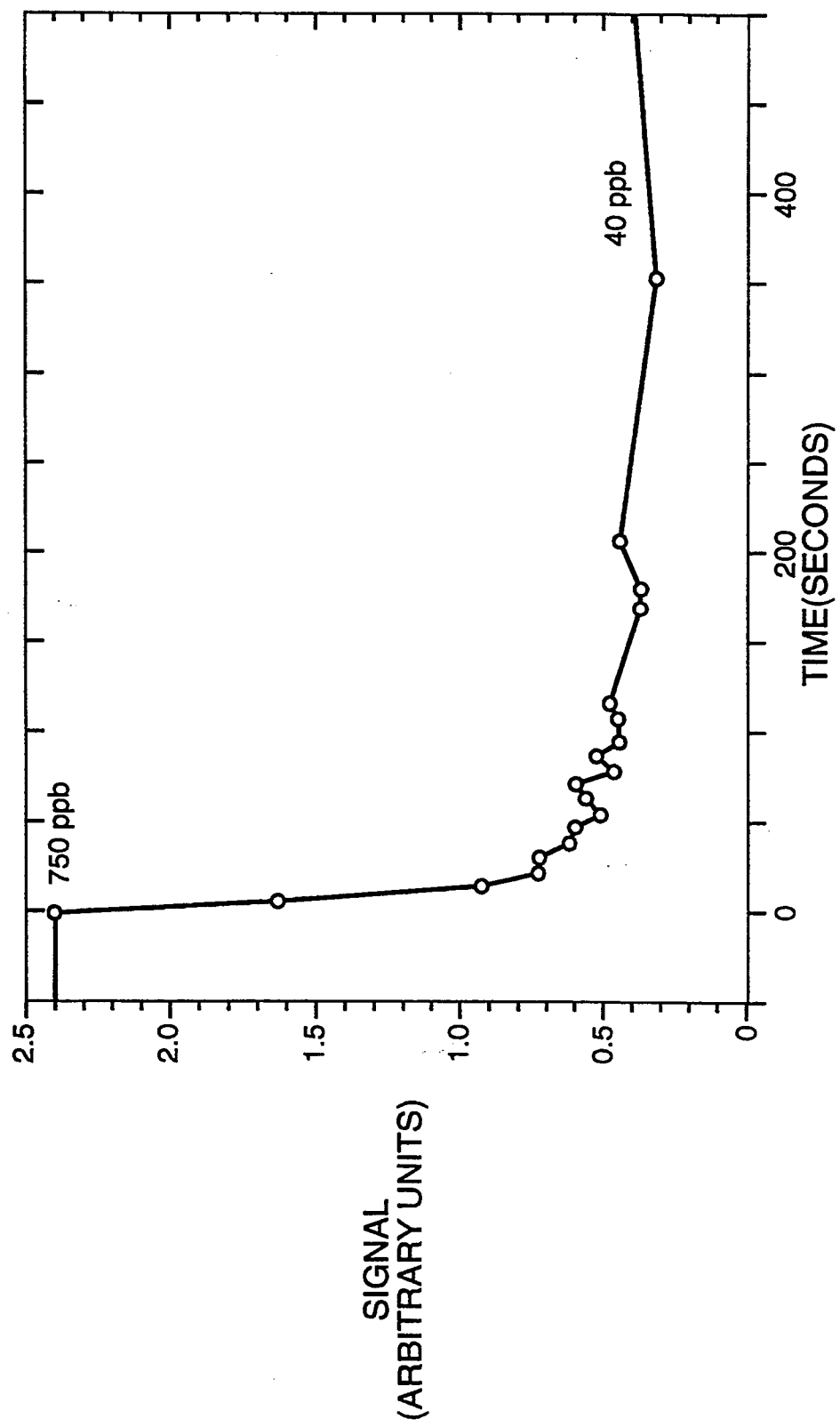
FIG._5

SPECTROSCOPIC CELL DESIGN

TECHNICAL FIELD OF INVENTION

The present invention deals with a spectroscopic sample cell for the analysis of trace impurities in sample gases. The present cell design is particularly applicable for the diode laser absorption spectroscopy detection of trace levels of water and other impurities commonly found in high purity gases.

BACKGROUND OF THE INVENTION

Spectroscopy is commonly used as a tool for analyzing impurities in gases. Significant problems persist, however, when the impurity of interest interacts with the surface of the sampling system and of the cell which is generally used to contain the sample during analysis. An impurity which absorbs on or reacts with the surface may appear lower in concentration than it really is. Alternatively, if the system has previously been exposed to the same impurity so that the impurity is reversibly bound to sampling cell surfaces, then the system may contribute impurity to the gases being analyzed so that the same may appear higher in concentration than that actually contained in the sample under investigation.

The detection of trace amounts of water in ultra high purity gases is particularly difficult. Background signals appear through moisture release from surfaces of the system. Moisture also tends to react with other components, and to adhere to surfaces. System considerations include spurious effects caused by cell wall absorption-desorption, atmospheric interference.

Many commercial applications require specialty gas such as semiconductor nitrogen gas to have certified water levels below 10 ppb. Small of amounts of impurities in such process gases have been shown to drastically effect both the yield of final products, especially when used in severe conditions including high temperature operations.

Accurate measurement techniques have been somewhat enhanced by taking precautions considered standard in trace moisture analysis, such as the use of high quality electropolished stainless steel for constructing the gas handling system while avoiding materials known to contribute large amounts of water vapor, such as certain polymers. In addition, the sample cell can be heated to remove absorbed water and by maintaining the cell at elevated temperatures, the speed of absorption/desorption processes can be increased and equilibrium reached more rapidly and with less sample gas being consumed. This procedure is somewhat inconvenient, however, and has never been demonstrated to be sufficient to reach trace moisture levels in the realm of 10 ppb.

As noted in an article entitled Multipass Absorption Cell Design For High Temperature UHV Operation, R. D. Shaffer, et al., Applied Optics Vol. 28, No. 9, pp. 1710-13 (May 1, 1989), tunable diode lasers have been employed in a heated multipass absorption cells to give a noise equivalent concentration below 10 ppb. However, in this work, calibration was effected using ppm level moisture standards and a reduced pressure ($10^{-3}$ torr) in the cell, whereas actual measurements are made at 10 torr in the cell. No data are presented on background moisture levels at this pressure. Obtaining adequately low and reproducible moisture levels under measurement conditions may be considered the principal difficulty in most problems of moisture measurement. The noise equivalent concentration quoted by Schaeffer et al. is characteristic primarily of the performance of their optical system (and, indeed, indicates a very good performance) and does not characterize fully the performance of the cell itself. No effort was made by Schaeffer et al. to optimize the flow pattern in their cell. In such a design, multimirrors are employed within the spectroscopic sample cell to effectively establish the sample cell volume within the system. Sample gases are passed within the cell while the analytical light beam is reflected multiple times to define the probe volume.

Spectroscopic techniques are frequently considered suitable for the analysis of reactive or corrosive gases because they rely on the interaction of a light beam, rather than any other physical probe, with the sample gas. This eliminates the possibility that an aggressive matrix gas will attack the sensor, producing erroneous readings or, at a minimum, reducing its lifetime. Spectroscopic techniques are also able to distinguish various impurities from one another on the basis of the wavelength of light at which interaction occurs with the impurity, so that no external separation means, (such as a chromatographic column) which might also be attacked by the matrix gas, is required.

Notwithstanding the above discussion, it is necessary, when using spectroscopic analytical techniques, to have a gas cell which can contain the sample gas and which is equipped with windows capable of transmitting the light being used. As noted above, for maximum analytical sensitivity, it is frequently also necessary that the cell be equipped with mirrors so that the light may pass through the sample cell more than once. In general, it is necessary to place these mirrors inside the cell where they are exposed to the matrix gas. If the sample gas reacts with the cell or its components, a reduction in performance can result should the windows or mirrors be obscured by deposits or the reaction products vapors into the gas phase. In particular, if reaction with the matrix gas leads to particulate deposits or to an increase in surface area it can be expected that the cell will exhibit an increased tendency to adsorb water vapor and subsequently release it, giving rise to considerable interference effects.

A solution to the above problems is generally approached by choosing cell and window materials which are relatively immune to the sample gas in question. For example, a corrosion resistant alloy such as Hastelloy is a good choice for a cell intended for HCl analysis. However, such alloys are expensive and the windows, mirrors and/or sealing and mounting materials used to place them in the cell may still prove vulnerable to attack. In addition, this approach does not specifically address interference and background difficulties which may arise as a result of outgassing, desorption or other release of moisture or other volatile materials from the cell surfaces. Although, as previously noted, heated cells have been employed to reduce adsorption/desorption problems, this approach is not always sufficient and may accelerate destructive interactions between the sample gas and the cell.

It is generally recognized that a cell with inlet and outlet at opposite ends is purged of impurities more efficiently than one in which both connections are at the same end, but this simple consideration is not sufficient to effectively purge all the important regions of the sample cell.

It has been determined that accurate trace impurity measurement is exceedingly difficult in light of the interactions as noted above between the gas and walls of the spectrographic cell. Problems resulting from such interactions are particularly acute when stable vortices occur in the flow field. The sole mechanism for purging these vortices is diffusion, a characteristically slow process. As such, if no stable vortices were to occur in the flow field, the entire cell would be continuously purged by the same gas minimizing cell wall interaction and greatly enhancing the opportunity for accurate trace impurity measurement.

It is thus an object of the present invention to provide a spectroscopic sample cell design which greatly enhances the opportunity for accurate trace impurity measurement.

Yet a further object of the present invention to provide a spectroscopic sample cell design which minimizes if not eliminates the creation of stable vortices within the flow field of the cell. These and further objects would be more readily appreciated when considering the following disclosure of appending drawings wherein:

FIG. 1 represents, in cross-section, the spectroscopic sample cell of the present invention;

FIG. 2 is a cross-sectional view of a spectroscopic sample cell showing the establishment of stable vortices by fluid dynamical simulation;

FIG. 3 depicts the cross-section of a spectroscopic sample cell produced according to the present invention in which the fluid dynamical simulation establishes an appropriate pattern exhibiting a lack of any established stable vortices, using an inlet flowrate characteristic of sampling rates typical of moisture analysis;

FIG. 4 illustrates, in cross-section, a preferred embodiment of the spectroscopic sample cell of the present invention; and FIG. 5 provides in graphical form, the results of cell performance in detecting a sudden change in moisture level.

SUMMARY OF THE INVENTION

The present invention is directed to a spectroscopic sample cell for the analysis of trace impurities in sample gases. The cell is provided with a gas inlet, gas outlet and a volume for confining said sample gases for analysis. The spectroscopic sample cell is further provided with two mirrors, a first mirror proximate the gas inlet and a second mirror proximate the gas outlet. The first mirror is provided with a hole at its radial center.

The spectroscopic sample cell is further characterized as having a conically-shaped cell profile substantially at the gas inlet having a diverging angle of less than approximately 30°. The location and sizes of the mirrors and conically-shaped cell profile are such as to substantially prevent the formation of vortices in the sample cell up stream of or in the region where the analysis of trace impurities is to take place.

DETAILED DESCRIPTION OF THE INVENTION

As previously noted, it is critical that the gas sample - surface interactions in the spectroscopic analysis cell be minimized. This can be done by establishing a geometrical profile of the cell such that gas which flows through the cell being probed by analytical light beams, experiences no vortices upstream of the probe volume or within it. Without being bound by any particular theory of operation, it is hypothesized that if a vortex exist in the gas cell, the gas in that region will be relatively stagnant and will accumulate impurities released from the cell walls. Diffusion processes for purging the vortex will increase the response time of the cell. The presence of such a vortex may be tolerable providing it is down stream of the probe volume and therefore has a minimal influence on the analysis.

Turning to FIG. 1, cell 10 is provided with confining side walls 11 defining a spectroscopic sample cell having a substantially circular cross-section. Cell 10 is provided with a gas inlet 12 and outlet 13 at opposite ends of the cell. The invention is to a multipass cell employing a first mirror 18 proximate to gas inlet 12 and a second mirror 20 proximate gas outlet 13. The mirrors reflect an appropriate light source which is caused to be reflected a multiple of times between said mirrors to define the probe volume.

Unless the location and relative geometry of the various elements of the spectroscopic sample cell are carefully established, stable vortices can be created. The location and relative geometry need to be placed based upon the desired flowrate to be used during moisture analysis. In this regard, reference is made to FIG. 2 whereby spectroscopic cell 30 is shown whereby mirrors 31 and 32 have been somewhat haphazardly placed within the spectroscopic cell. As a result of boundary layer separation experienced by the sample gas through introduction at inlet 34, a stable vortex is shown by fluid dynamic simulation at 33. This obviously provides an unacceptable cell design. The design in FIG. 2 is by no means the worst which can be imagined with a similar configuration. Small variations in the hole size in mirror 31 and/or in its size can lead to formation of vortices between the mirrors, where their effect will be maximized.

In light of the above discussions, simply providing a conically-shaped inlet and pair of mirrors located within the sampling cell alone is insufficient to provide the desired cell performance. As such, this basic configuration was subjected to numerical simulation of the fluid dynamics in the cell. In referring to FIG. 1, it was determined that the divergent angle $\theta$ be less than 40° and preferably approximately 10° half angle, 20° total, forming a nozzle 14 by diverging sidewalls 15 and 16. Divergence continues so that the nozzle expands to approximately 50% of cell diameter at which point the conically-shaped inlet abuts to the cell's full diameter at edge 17.

First mirror 18, having a circular cross-section, is provided with a hole its radial center. In complying with appropriate design criteria, hole 19 should have a diameter c less than inlet diameter a. Further, the diameter d of mirror 18 should be greater than the diameter j at the widest point of conically-shaped inlet 14. Finally, diameter d of first mirror 18 should be such that free cell cross-sectional area at the plane at which first mirror 18 is located and which is unoccupied by said first mirror is greater than the cross-sectional area a at gas inlet 12. In other words $a^2 < (f^2 - d^2)$.

It is a design goal of the present spectroscopic sample cell that the first mirror is positioned and sized such that substantially all of the gas passing through the cell proceeds around the first mirror without separating into multiple stream paths. It is also intended that hole 19 in mirror 18 be sized to allow the passage of sufficient gas to pass there through in order to purge an area downstream of said first mirror as gas passes within cell 10 in the direction of arrow 21. These design criteria can be optimally met by providing first mirror 18 as being approximately 4/7ths of the overall cell diameter f and providing second mirror 20 having diameter e which is, in turn, approximately 5/7th of the cell diameter f. Appropriate purging behind first mirror 18 can be carried out without vortex formation by ideally sizing diameter c of hole 19 to be approximately 1/28th of the overall cell diameter f. In addition, it has been found that optimum results were achievable when first mirror 18 is spaced from the end of nozzle 14 at a distance h which is equal to approximately ¼ cell diameter f. A preferred cell design embodiment is shown in FIG. 4 whereby cell 50 is provided with confining sidewalls 11 defining a spectroscopic sample cell having a substantially circular cross-section. Cell 50 is provided with a collimated beam of light. The beam enters the cell through input window 59 and, after reflection from input mirror 54, is passed into the main body of cell 50 through aperture 53 in first multi-pass mirror 52. The beam makes many passes through the cell volume, following a path determined by the curvature and separation of mirror 52 and 57 which are placed according to the design of Herriot. In this regard, the gas sample is introduced to cell 50 through inlet 55 and through conically-shaped inlet 56. Subsequent to analysis, the gas is caused to pass from spectroscopic sample cell 50 through outlet 58 which is, in turn, functionally connected to appropriate pumping equipment (not shown).

After the appropriate light beam makes its various passes through the cell volume, it exits the cell through the same aperture and window 59 and strikes a detector outside the cell (not shown). A variety of modulation and signal averaging techniques can be applied to the source and detection system to improve its sensitivity and robustness with respect to outside source interference.

When appropriate design criteria are followed, the fluid dynamic simulation as shown in FIG. 3 presents itself noting the lack of any stable vortices as a result of gas being introduced at inlet 41 within cell 40.

FIG. 5 illustrates the performance of the spectroscopic cell of FIG. 4 when used to detect a sudden change in moisture level. The data used to generate the graph presented as FIG. 5 were obtained using a nitrogen carrier gas. However, the same performance may be expected in more aggressive matrices. The time to reach the background level from 750 ppb is approximately 2 minutes which should be considered short compared to other spectroscopic methods and even compared with fast, non-spectroscopic methods. The background level demonstrated in FIG. 5 is approximately 40 ppb but this is not considered the ultimate limit of the present approach which is also limited by other features particular to this embodiment which are capable of independent improvement. For example, the ambient moisture level of air outside the cell could be adjusted.

We claim:

1. In a spectroscopic sample cell for the analysis of trace impurities in sample gases having a gas inlet, a gas outlet and a volume for confirming said sample gases for analysis, the improvements comprising:
    (a) providing two mirrors, a first mirror proximate the gas inlet and a second mirror proximate the gas outlet, said first mirror having a hole at its radial center;
    (b) providing a conically-shaped cell profile substantially at said gas inlet, the diverging angle of said profile being less than approximately 40°; wherein the location and sizes of said mirrors and conically-shaped cell profile are such as to substantially prevent the formation of vortices in said sample cell upstream of or in the region where said analysis of trace impurities takes place.

2. The spectroscopic sample cell of claim 1 wherein said first mirror is positioned and sized such that substantially all of the gas passing through said sample cell proceeds around said first mirror without separating into multiple stream paths.

3. The spectroscopic sample cell of claim 1 wherein said hole in said first mirror is sized so as to allow the passage of sufficient gas to purge an area downstream of said first mirror.

4. The spectroscopic sample cell of claim 1 wherein said cell and mirrors are substantially circular in cross-section.

5. The spectroscopic sample cell of claim 4 wherein the hole in said first mirror is smaller than the gas inlet to said cell.

6. The spectroscopic sample cell of claim 4 wherein said first mirror is spaced less than approximately four gas inlet diameters from the downstream end of said conically-shaped cell profile.

7. The spectroscopic sample cell of claim 4 wherein the diameter of the first mirror is greater than the diameter of said cell at the downstream end of said conically-shaped cell profile.

8. The spectroscopic sample cell of claim 4 wherein said first mirror is sized such that the free cell cross-sectional area at the plane at which said first mirror is located unoccupied by said first mirror is greater than the gas inlet cross-sectional area.

9. The spectroscopic sample cell of claim 4 wherein said first mirror is approximately 4/7 of the cell diameter.

10. The spectroscopic sample cell of claim 4 wherein said second mirror is approximately 5/7 of the cell diameter.

11. The spectroscopic sample cell of claim 4 wherein the hole in said first mirror is approximately 1/28 of the cell diameter.

12. The spectroscopic sample cell of claim 4 wherein said first mirror is spaced from the downstream end of said conically-shaped cell profile by a distance equal to approximately ¼ of the cell diameter.

13. The spectroscopic sample cell of claim 1 wherein said diverging angle of said conically-shaped cell profile is approximately 20°.

14. The spectroscopic sample cell of claim 13 wherein said conically-shaped cell profile expands to approximately 50% of the cell diameter.

* * * * *